(12) United States Patent
Hahn

(10) Patent No.: US 6,475,503 B2
(45) Date of Patent: Nov. 5, 2002

(54) METHODS OF USING WORM CASTINGS FOR INSECT REPELLENCY

(76) Inventor: George E. Hahn, 205 Liszi Ave., Cardiff by the Sea, CA (US) 92007

(*) Notice: Subject to any disclaimer, the term of this patent is extended or adjusted under 35 U.S.C. 154(b) by 0 days.

(21) Appl. No.: 09/784,283

(22) Filed: Feb. 16, 2001

(65) Prior Publication Data

US 2002/0090669 A1 Jul. 11, 2002

Related U.S. Application Data

(60) Provisional application No. 60/187,243, filed on Mar. 3, 2000.

(51) Int. Cl.$^7$ .................... A01N 25/00; A61K 35/36
(52) U.S. Cl. ..................... 424/405; 424/543; 71/65
(58) Field of Search .................. 424/405, 543; 71/65

(56) References Cited

U.S. PATENT DOCUMENTS

| | | | | |
|---|---|---|---|---|
| 4,147,256 A | * | 4/1979 | Kiss et al. | |
| 4,194,320 A | * | 3/1980 | Svirklys | |
| 5,082,486 A | * | 1/1992 | Glogowski | |
| 5,211,980 A | * | 5/1993 | Cox | |
| 5,597,946 A | * | 1/1997 | Jaynes et al. | |
| 5,633,450 A | | 5/1997 | Suslow et al. | |

FOREIGN PATENT DOCUMENTS

| | | | |
|---|---|---|---|
| AU | DW 2000-013398 | * | 11/1999 |
| NL | DW 1986-160609 | * | 5/1986 |

OTHER PUBLICATIONS

Linda McGraw, New Plants Put a Hurt on Pests, Feb. 18, 1999.

* cited by examiner

Primary Examiner—Christopher R. Tate
Assistant Examiner—Randall Winston
(74) Attorney, Agent, or Firm—Don E. Erickson

(57) ABSTRACT

The present invention describes a material and a method for repelling insects. The method consists of disposing a naturally formed chitinase about an area to be protected. The naturally formed chitinase is produced from worm castings and the worm castings may be disposed naturally, in the form of timed-release pellets, or in a liquid form. The area to be protected includes plants and structures. The naturally formed chitinase may be disposed about the base of the plant or structure, or on the leaves of the plant.

12 Claims, 2 Drawing Sheets

METHODS OF USING WORM CASTINGS FOR INSECT REPELLENCY

This application is based on provisional patent application Ser. No. 60/187,243 filed Mar. 3, 2000, entitled, "Methods of using worm castings for insect repellency.

BACKGROUND OF INVENTION

1. Field of the Invention.

This invention describes a method of producing a biodegradable insect repellant, and more particularly to a method of using natural chitinase as an insect repellant.

2. Description of the Related Art.

Worm castings have been known as being very beneficial to promote plant growth for more than 100 years but they have not been know to be effective for insect pest repellency applications. Research by Ohio State University testing for the recommended application rate of worm castings for highest growth improvement recommended a 10%–20% mix. The rule given by Ohio State University to achieve these percentages was that a ½ inch layer worked into the soil will provide a 10% ratio and a 1-inch layer worked into the soil will provide a 20% ratio.

U.S. Pat. No. 6,245,551 to Suslow describes a method of treating or protecting plants, fruit and roots from fungal infections comprising the step of applying an effective amount of an antibiotic-producing bacillus. Tests performed Suslow showed a systemic entrance of the chitinase-producing organisms when these were applied to the soil around the plants. Suslow did not disclose the use of chitinase as an insect repellant.

An article by Linda McGraw, *New Plants Put a Hurt on Pests,* published Feb. 18, 1999, describes the genetic engineering of tobacco plants by the injection of artificially produced chitinase. Plant material then consumed by insects causes the chitin of the insect to break down, making such insect subject to disease by microorganisms. The McGraw article did not describe the use of chitinase as an insect repellent.

Using worm castings to repel various insects has many advantages. Worm castings are non-toxic so provide a non-poisonous alternative to chemical pest treatments. The non-toxic nature of worm castings means the use should not harm other valuable organisms found in soil. The fact that worm castings are a natural element found in healthy soil indicates that harmful side effects should be limited. The elements found naturally in worm castings, which appear to be the active elements to repel insects, are living organisms. This means that the repellency could be provided for a longer time period unless the organisms are killed from a different source.

BRIEF SUMMARY THE INVENTION

The present invention deals with using worm castings as an insect repellent as a layer on the ground for walking insects, incorporated into the soil feeding plants for pest insects, incorporated into the feeding liquid for hydroponic growing, and as liquid worm castings sprayed onto the leaves of plants for a topical treatment. The worm castings can be used on soil, turf, or in hydroponic applications.

It was observed that ants refused to cross a layer of worm castings. When a layer of worm castings was put around a tree or bush the reaction of the ants was immediate. Ants in the tree or bush congregate in an agitated manner just above the border of the worm castings. Soil that ants will easily cross tested at less than 1 million CFU/gdw (Colony Forming Units/gram dry weight). This supports that ants can detect and are averse to a level of chitinase somewhere between 1 and 54 million CFU/gdw. Red fire ants are particularly averse to an application of worm castings. Testing has shown that red fire ants will abandon their nests within 24 hours with a ¼ inch application over and around the nest mound.

Testing was done on many plants to determine if worm castings are able to change the level of chitinase in the leaves of plants. This invention describes a method of using worm castings in various methods to activate the natural insect repellency produced by the chitinase-producing organisms found naturally in plants. The concentration of chitinase must be sufficiently high to repel insects. Testing has shown that the natural level of chitinase found in most plants is often not sufficient to repel insects. Worm castings are the feces or excrement from the common red earthworm found in much of the world. The genus of the red earthworm worm is *eisenia foetida*. Other genus of the earthworm also provide worm castings suitable for this invention. Worm castings are produced as a normal part of the worm life cycle when worms are fed a diet of various forms of biodegradable materials such as compost, paper, food waste, and any other degradable organic material. Worm castings can be used to increase the level of chitinase to a repulsion level. Liquid worm castings can be used as a foliar spray to administer a concentration of chitinase topically to the leaves and stems of plants. Liquid worm castings give a temporary repellency effect that can be effective to keep the insects away until the level of natural repellency is increased in the nectar of the plant. Worm castings can be added to soil to repel walking insects such as ants and including red fire ants. Worm castings can also be added to the hydroponic feed liquid for plants to increase natural level of chitinase production and possible other natural element to repel insects. Worm castings contain various organisms that produce enzymes known as various forms of chitinase to which insects have a strong aversion. Worm castings are called by several other names: vermi-compost, vermi-castings, worm droppings, worm manure and others. All of these terms refer to the same material.

DETAILED DESCRIPTION OF THE INVENTION

Figure 1:
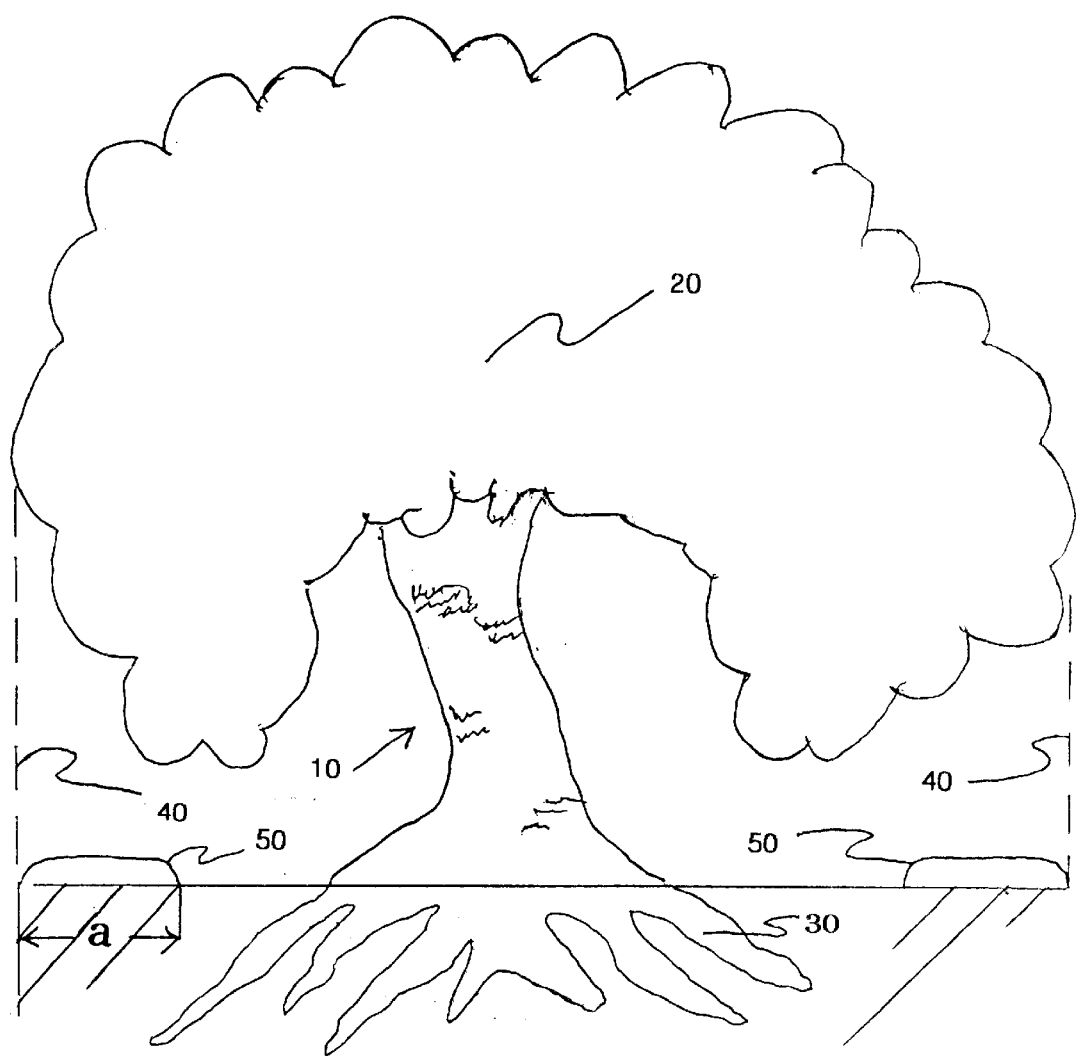
FIG. 1 is a two-dimensional drawing of a tree, showing its underground root structure.
Figure 2:
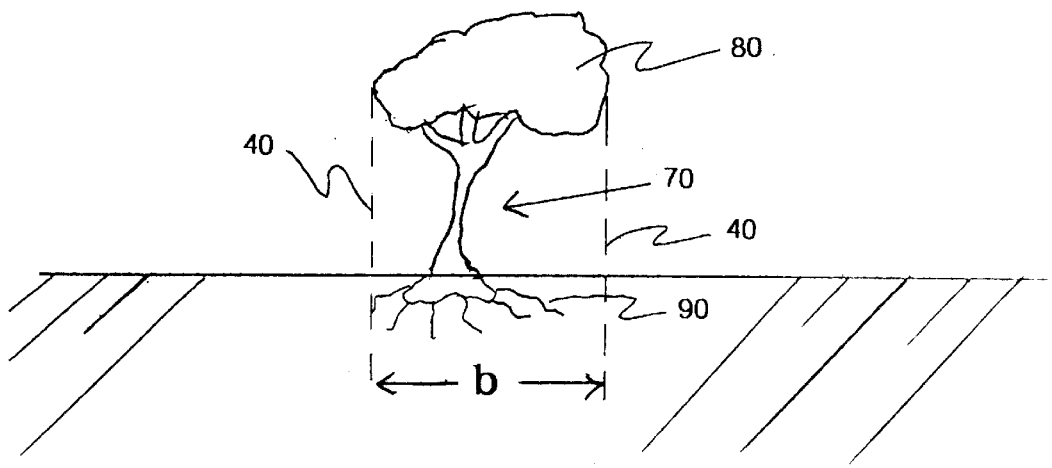
FIG. 2 is a two-dimensional drawing of a bush, showing its underground root structure.

FIG. 1 depicts a tree 10, having a leaf area 20 and a root structure 30. The outer limits of leaf area 20 describe drip line 40, which extends the periphery of tree 10. Extending inwardly from drip line 40 toward a point over the root structure for a distance a about the tree is the feeder root zone with worm castings 50 disposed above the feeder root zone. Referring now to FIG. 2, bush 70 has a leaf area 80, a root structure 90, drip line 40, and feeder root zone comprising the area of the ground below the circumference of leaf area 80 of diameter b. Research has discovered that one natural insect repellant is any chitinase enzyme. The exact minimum level of chitinase for detection and aversion by an insect has not been definitively determined.

Hibiscus leaves that were covered in white fly cocoons were tested and found to have a level of chitinase at 300,000 CFU/gdw. The white fly infested hibiscus plants were treated with worm castings. Worm castings were applied in a ½ inch layer from the bases, or stems, to drip line 40 (FIG. 2). In about two months all white fly residue and cocoons were gone. White flies from neighboring plants, which had not been treated, would fly around the treated leaves but not land on these leaves. Other plants, including trees, have been tested to determine if the use of worm castings is effective to repel spider mites, aphids, bark beetles, psylids, and other insects. Referring again to FIG. 1, worm castings 50 are disposed about the periphery of tree 10 in the feeder zone. With worm castings 50 in the feeder zone of a plant or tree, effective repellency has been seen in such plants and tree against various insects. Spider mites will leave a plant in about two weeks. Aphids will leave in about six weeks. Bark beetles will leave trees after several months. The time period for the insects to leave a plant appears dependent on the size of the plant.

Ants leave their nests within 24 hours and do not return for some period of time. The exact length of time for abandonment must be tested and will no doubt be dependent on other environmental conditions. Ants will not cross a layer of worm castings 50 for about two weeks, and then will gingerly begin to cross. If the top layer of worm castings 50 is raked, then the ants will again refuse to cross. Using worm castings in all soil areas around a home appears to repel the ants for many months. The exact time will need to be tested and will no doubt be dependent on other environmental conditions. The repellency effect for pest insects takes a period of time to begin, once the level of chitinase has been increased to repellency level, the insects leave the plant.

The level of the chitinase producing microorganisms for effective repellency is in the range of 1 million CFU/gdw. Worm castings were tested to determine the level of the chitinase enzyme production. Tests of worm castings show concentrations of chitinase producing microorganisms in the range of 54 million CFU/gdw. This is concentration is over 50 times the estimated level required for repellency. The chitinase-producing organisms in the worm castings consisted of five bacteria, four fungi, and five actinomycetes. The leaves from the treated hibiscus were tested for chitinase four months after the initial application of worm castings. This test revealed that the level of chitinase producing organisms had increased to 670 million CFU/gdw. The chitinase producing organisms found in the leaves were two bacteria that were not any of the five found in the worm castings. This indicates that some trigger element in the worm castings activates multiplication of the organisms that produce the enzyme chitinase. The time period for effectiveness is at least six months. As above, the exact time period will need to be tested and will be dependent on other environmental conditions.

Figure 3:
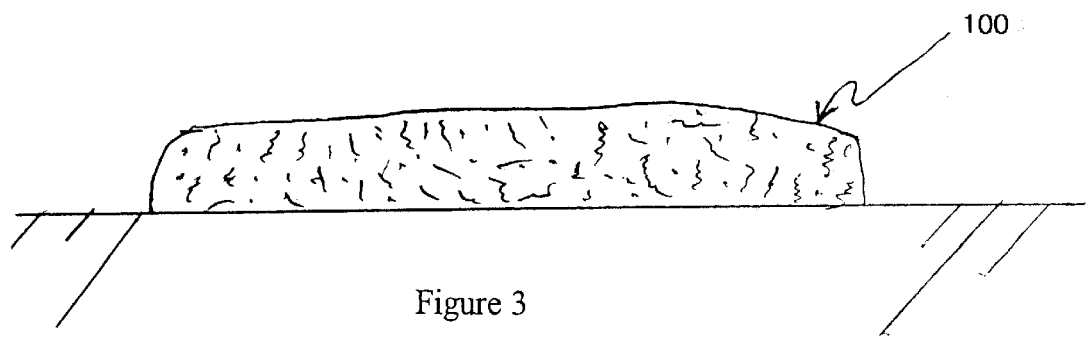
FIG. 3 is a cutaway view of a worm bed.
Figure 4:
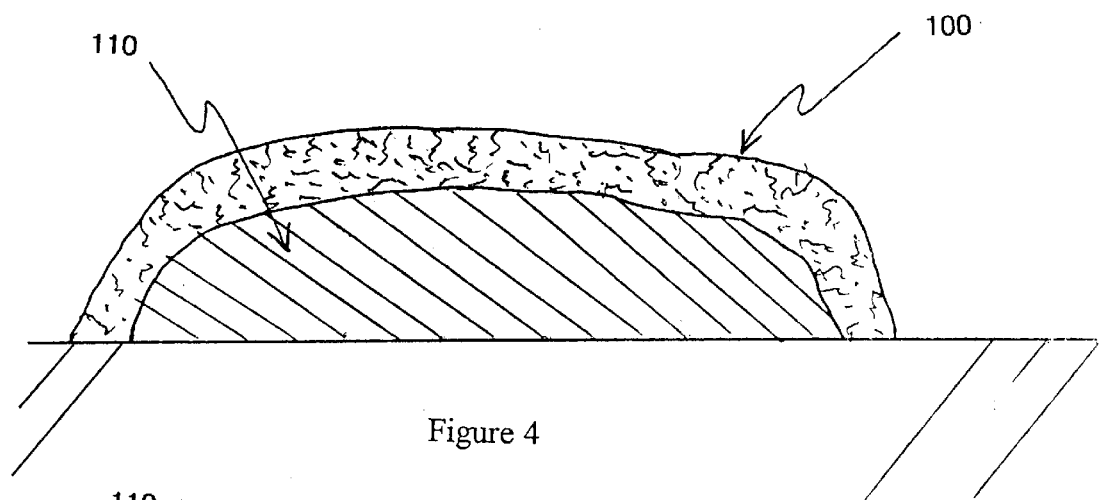
FIG. 4 is a cutaway view of a worm bed with worm castings.
Figure 5:
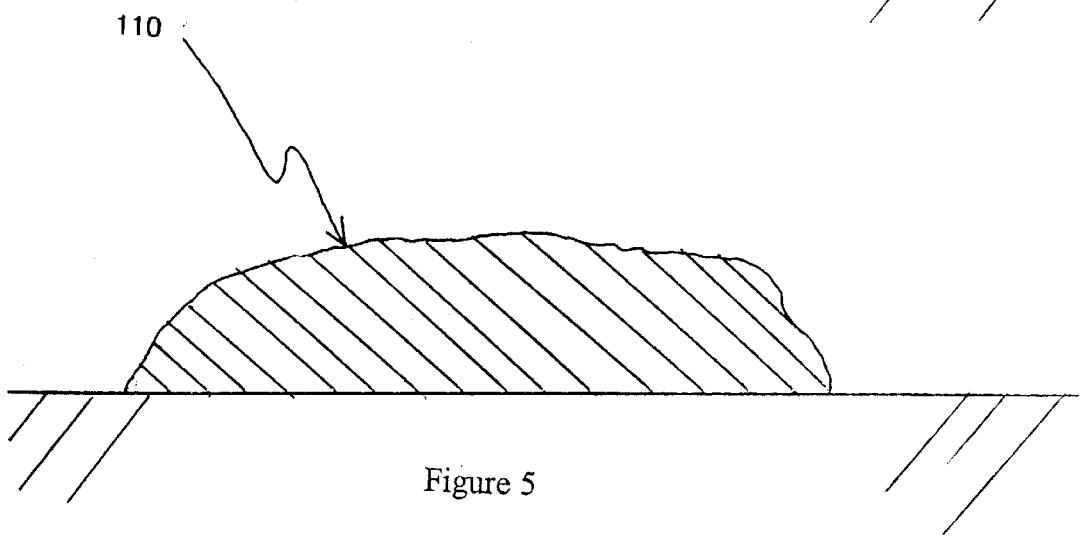
FIG. 5 is a cutaway view of the worm castings at harvest time.

The science of worm husbandry is well known. FIGS. 3, 4 and 5 depict a worm bed through harvesting of the worm castings. Reference is made to FIG. 3 where worm bed 100 is disposed on the ground. Worm castings are produced by feeding worms various forms of waste biomass. This provides the advantage that worm castings do not require the consumption of valuable natural resources. The production instead consumes waste materials. Worm bed 100 comprises a layer of biomass with earthworms disposed therewithin.

FIG. 2 depicts worm bed 100, with worm castings 110 disposed under worm bed 100. The earthworms are fed approximately 4 inches of biomass per week, and after feeding the worms move to the top of worm castings 110 to defecate, moving back into the biomass to continue feeding. When the depth of worm castings 110 grows to a depth of 3 feet (FIG. 4), worm bed 110 is removed, leaving the processed worm castings 110 (FIG. 5).

Worm castings can be supplied in the natural granular form, pelletized for time release, and liquefied. Liquid worm castings are produced by soaking worm castings in water for at least 24 hours, leaching the chitinase from the castings, then removing the liquid. Liquid castings are also produced naturally by the worms while feeding. The liquid can be collected from the bottom of the worm beds. Liquid worm castings are also referred to as: worm tea, worm castings tea, vermi-tea, and other similar terms. Liquid worm castings have been sprayed onto the leaves of plants infested by various insects. The evidence indicates that this provides a temporary repellency for a variety of insects. This would be expected since the liquid worm castings has a level of chitinase producing organisms similar to the level found in the granular form of worm castings.

While the present description contain many specificities, these should not be construed as limitations on the scope of the invention, but rather as an exemplification of some preferred embodiments thereof.

For example, the insect repellant of the invention may be used to repel walking insects from invading a structure, such as a house, by applying the insect repellant around the periphery of the structure on the ground adjacent its base, or foundation.

I claim:

1. An insect repellant consisting of isolated worm castings, whereby the worm castings consist of chitinase producing microorganisms at a level of at least 1 million CFU/gdw (Colony Forming Units/gram dry weight).

2. The insect repellant of claim 1 wherein the isolated worm castings are in form of a timed-released pellet.

3. The insect repellant of claim 1 wherein the isolated worm castings are in a liquid state.

4. A method for repelling insects, the method consisting of disposing an effective amount of worm castings about an area in need of insect protection, wherein the level of chitinase producing microorganisms within the worm casting is at least 1 million CFU/gdw (Colony Forming Units/gram dry weight).

5. The method of claim 4 wherein the step of disposing the worm castings about an area to be protected includes the step of forming the worm castings into time-release pellets.

6. The method of claim 4 wherein the step of disposing the worm castings about an area to be protected includes the step of forming the worm castings in a liquid.

7. The method of claim 4 wherein the area to be protected is a plant, the plant having a base and a leaf area, and the step of disposing the worm castings about the plant includes the step of disposing the worm castings on the leaf area of the plant.

8. The method of claim 7 wherein the step of disposing the worm castings on the leaf structure includes disposing the worm castings in the form of timed-release pellets.

9. The method of claim 7 wherein the step of disposing the worm castings on the leaf area of the plant includes disposing the worm castings in liquid form.

10. The method of claim 7 wherein the plant additionally includes a root structure, a drip line, and a feeder root zone between the drip line and the base of the plant and the step of disposing the worm castings about the plant includes disposing the worm castings on the feeder root zone.

11. The method of claim 4 wherein the area to be protected is a structure, the structure having a base, and the step of disposing the worm castings about the structure includes the step of disposing the worm castings on the ground adjacent the base of the structure.

12. The method of claim 4 wherein the worm castings are hydroponically disposed about the area to be protected.

* * * * *